United States Patent [19]

Kiefer

[11] 4,402,882

[45] Sep. 6, 1983

[54] PROCESS FOR THE PRODUCTION OF DIPHOSPHASPIRO COMPOUNDS

[75] Inventor: Jürg Kiefer, Reinach, Switzerland

[73] Assignee: Ciba-Geigy Corporation, Ardsley, N.Y.

[21] Appl. No.: 295,170

[22] Filed: Aug. 21, 1981

[30] Foreign Application Priority Data

Sep. 2, 1980 [CH] Switzerland .......................... 6605/80

[51] Int. Cl.$^3$ ................................................. C07F 9/40
[52] U.S. Cl. ................................ 260/980; 260/927 R; 260/988
[58] Field of Search ......................................... 260/980

[56] References Cited

U.S. PATENT DOCUMENTS 3,141,032 7/1964 Friedman ........................ 260/927 R
3,391,229 7/1968 Cherbuliez et al. ................. 260/980

OTHER PUBLICATIONS

Houben-Weyl, Band XII/1, (1963), p. 612.
Honig et al., "J. Org. Chem.", vol. 42, No. 2, (1977), pp. 379-381.
Cherbullez et al., "Helvetica Chimica Acta", vol. XLVI, Fasciculus VI, (1963), No. 275, pp. 2461-2464.

Primary Examiner—Anton H. Sutto
Attorney, Agent, or Firm—Harry Falber

[57] ABSTRACT

The reaction of phosphonic acid or a phosphonic acid ester of the formula II

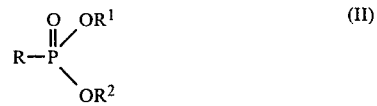

with a phosphonic acid dichloride of the formula III

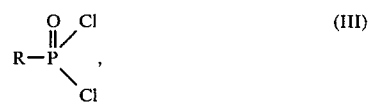

wherein R, R$^1$ and R$^2$ are as defined in claim 1, gives a phosphonic anhydride of the formula IV

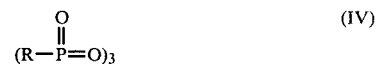

which, with or without being isolated from the reaction solution, is reacted with pentaerythritol, in the temperature range from 60° to 120° C., to give a compound of the formula I

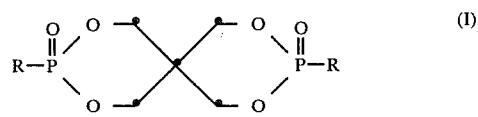

the molar ratio of anhydride of the formula IV to pentaerythritol being about 2:1.

4 Claims, No Drawings

PROCESS FOR THE PRODUCTION OF DIPHOSPHASPIRO COMPOUNDS

The present invention relates to a process for the production of diphosphaspiro compounds from an alkyl- or aryl-substituted phosphonic acid or an alkyl- or aryl-substituted phosphonic acid ester, an alkyl- or aryl-substituted phosphonic acid dichloride and pentaerythritol. The diphosphaspiro compounds obtainable by the process of this invention are known compounds and have attained importance in particular as flameproofing agents for polymers.

The known methods of obtaining diphosphaspiro compounds have the disadvantage that they either require relatively complicated apparatus to perform them or they only give unsatisfactory yields.

For example, U.S. Pat. No. 3,141,032 describes the production of spirodiphosphonates from the corresponding spirodiphosphites by the Arbuzov rearrangement, in the presence of a suitable catalyst. Temperatures of 175° to 200° C. are required for this rearrangement, so that the process has to be carried out in an autoclave or a bomb tube.

The preparation of a spirodiphosphonate from phenylphosphonic acid dichloride and pentaerythritol is described in Example 4 of German Offenlegungsschrift No. 2 836 771, the phenyl-substituted spirodiphosphonate being obtained in a yield of 69.3%. A number of experiments have shown that, under identical reaction conditions and using methylphosphonic acid dichloride, the methyl-substituted spirodiphosphonate is obtained instead of the phenylphosphonic dichloride in yields of only 30 to 40%.

The Journal of Organic Chemistry, Vol. 42, No. 2 (1977), pages 379–381, describes the transesterification of diphenylmethylphosphonate with pentaerythritol at 192°–205° C., to give the corresponding diphosphaspiro compound in a yield of 52%. In addition to the unsatisfactory yield, this process also has the drawback that the phenol obtained during the transesterification has to be removed from the reaction mixture in vacuo at 120°–200° C.

From Helvetica Chimica Acta, Vol. 46 (1963), pages 2461–2464, it is known that the esterification of e.g. methanephosphonic anhydride with both propanol and propanediol yields in each case the methanephosphonic acid monoester.

It has now been found that the reaction of an alkyl- or aryl-substituted phosphonic acid, or an ester thereof, with an alkyl- or aryl-substituted phosphonic acid dichloride to give the corresponding phosphonic anhydride, and subsequent reaction of this latter with pentaerythritol, gives the corresponding diphosphaspiro compound in higher yields.

Accordingly, the present invention provides a process for the production of diphosphaspiro compounds of the formula I

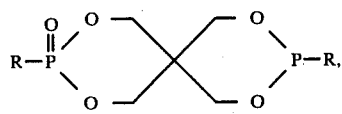

wherein each R independently is alkyl of 1 to 6 carbon atoms, phenyl, benzyl or cyclohexyl, but preferably each has the same meaning and is in particular methyl, which process comprises reacting a phosphonic acid or a phosphonic acid ester of the formula II

wherein R has the same meaning as in formula I and each of $R^1$ and $R^2$ is a hydrogen atom, methyl or ethyl, with a phosphonic acid dichloride of the formula III

wherein R has the same meaning as in formula I, in equimolar amounts in an organic solvent or using an excess of the phosphonic acid ester of the formula II, in the temperature range from 50° to 120° C., preferably from 80° to 100° C., to give a phosphonic anhydride of the formula IV

and subsequently reacting the anhydride of the formula IV, preferably without isolating it from the reaction solution, with pentaerythritol, in the temperature range from 60° to 120° C., preferably from 80° to 100° C., to give a compound of the formula I, the molar ratio of anhydride of the formula IV to pentaerythritol being about 2:1.

The compounds of the formula II and III are also known compounds. Thus the phosphonic acid chlorides of the formula III can be obtained from the dialkyl phosphonates by reaction with thionyl chloride. Such reactions are described e.g. in U.S. Pat. Nos. 2,847,469 and 4,213,922. The preparation of the phosphonates is described e.g. in "Organic Reactions" 6 (1951), page 273.

The reaction of a phosphonic acid or phosphonate of the formula II with a phosphonic acid dichloride of the formula III can be carried out in the presence or absence of an inert organic solvent. Examples of suitable solvents are: aromatic hydrocarbons such as toluene and xylene, halogenated aromatic hydrocarbons such as chlorobenzene and o-dichlorobenzene, halogenated aliphtic hydrocarbons such as dichloroethane, trichloroethane and tetrachloroethane or, preferably, dioxane. It is also possible to use an excess of phosphonate as solvent.

The process of this invention can be carried out both continuously and discontinuously, i.e. the phosphonic anhydride of the formula IV obtained in the reaction of a phosphonic acid or a phosphonate of the formula II with the phosphonic acid dichloride of the formula III, can also be reacted with the pentaerythritol without first being isolated from the reaction solution.

In the continuous process, the pentaerythritol can be added at the outset to the starting materials employed for the formation of the phosphonic anhydride. In this procedure the pentaerythritol is suspended together with the phosphonic acid or phosphonate of the formula II in an inert solvent, and the phosphonic acid dichloride is added dropwise over the course of 1 to 2 hours at 50°–120° C., preferably at 80°–100° C.

When preparing the dimethyl-substituted diphosphonospiro compound by this process it can be advantageous to dispense with the inert solvent by suspending the pentaerythritol in the phosphonate. In this case an excess of phosphonate is used.

The molar ratio of the starting materials is so chosen that at least 3 moles of phosphonic acid or phosphonate, where appropriate an excess thereof, and 3 moles of phosphonic dichloride, are used per mole of pentaerythritol.

Hydrogen chloride or methyl or ethyl chloride escapes continually during the course of the reaction and the pentaerythritol goes into solution after a short time. The diphosphaspiro compound of the formula I begins to precipitate from the reaction solution even before the addition of the phosphonic acid chloride is complete. After addition of the phosphoric acid dichloride, the reaction solution is stirred for 2 to 3 hours at the reaction temperature and the suspension is then cooled to room temperature. The resultant dense crystal slurry is diluted with an organic solvent, e.g. acetone, methanol or propanol, and then filtered, affording the pure diphosphaspiro compound in a yield of more than 70%.

In the discontinuous process, the anhydride formed by reacting equimolar amounts of phosphonic acid or phosphonate of the formula II with phosphoric acid dichloride of the formula III, is isolated from the reaction solution. The anhydride is obtained by adding an inert solvent when gas has ceased to evolve from the reaction solution. It precipitates in the form of white crystals, which are isolated by filtration.

To react the anhydride with the pentaerythritol, the anhydride is suspended in an inert solvent or in the phosphonate, and the pentaerythritol is added, in portions, over the course of about 15 to 30 minutes at 60°–120° C., preferably at 80°–100° C., such that the molar ratio of phosphonic anhydride to pentaerythritol is about 2:1. When the addition of pentaerythritol is complete, the reaction is allowed to go to completion for about 1 hour at the reaction temperature. The reaction solution is then cooled to room temperature, whereupon the diphosphaspiro compound of the formula I precipitates and is isolated by filtration. The compound is purified by the same procedure as employed in the continuous process.

The invention is illustrated by the following Examples.

EXAMPLE 1

A 4 liter sulfonating flask, equipped with stirrer, thermometer, cooler with gas outlet pipe and dropping funnel, is charged with 272 g (2 moles) of pentaerythritol and 1 liter of dimethyl methylphosphonate, and the mixture is heated to 70°–80° C. Then 798 g (6 moles) of methylphosphonic acid dichloride are dropped into the thin white suspension. Methyl chloride escapes continually and the pentaerythritol goes into solution. Before the addition of the acid chloride is complete, pure spirophosphonate precipitates from the reaction solution. When the addition is complete, the reaction mixture is stirred for 3 hours at 80°–90° C. and then cooled to room temperature. The dense crystal slurry is diluted with 500 ml of methanol and the product is collected on a suction filter with cloth filter. The filter residue is washed with cold methanol, filtered well with suction, and dried in a vacuum drying cabinet at 80° C. Yield of spirophosphonate: 390 g (76.1% of theory) of white, glistening crystals with a melting point of 247.5°–249° C.

Elemental analysis: calculated: C 32.83%, H 5.51%, P 24.19%; found: C 32.75%, H 5.46%, P 24.11%.

EXAMPLE 2

(a) A sulfonating flask, equipped with stirrer, thermometer, dropping funnel and gas outlet pipe, is charged with 532 g (4 moles) of methylphosphonic acid dichloride, which are then heated to 60°–70° C. Then 520.8 g (4.20 moles) of dimethyl methylphosphonate are slowly added dropwise over 2 hours. Intense evolution of gas begins immediately, subsides after 3 hours, and is complete after 4 hours. Then 60 ml of anhydrous acetone are added dropwise to the resultant clear viscous oil over 20 to 30 minutes. The solution becomes turbid, the anhydride precipitates, and a white, fine suspension forms. This suspension is cooled to room temperature and filtered over a glass suction filter. The filter residue is washed with anhydrous acetone, well filtered with suction, and dried in a vacuum drying cabinet at 80° C.

Yield of $[CH_3PO_2]_3$: 536 g (85.9% of theory) of a white crystalline powder with a melting point of 145°–146° C.

Elemental analysis: calculated: C 15.40%, H 3.88%, P 39.71%; found: C 15.33%, H 4.01%, P 39.56%.

(b) A 350 ml sulfonating flask, equipped with stirrer and thermometer, is charged with 93.60 g (0.4 mole) of methylphosphonic anhydride ($[CH_3PO_2]_3$) and 100 ml of dimethyl methylphosphonate. The suspension is heated to 70° C. and 27.20 g (0.20 mole) of pentaerythritol are added in portions over 10 minutes. The temperature rises to 110° C. and the entire contents of the flask go into solution. When the addition is complete, the spirophosphonate precipitates from the reaction solution. The batch is stirred for 1 hour at 80°–90° C., then cooled to room temperature, and the precipitate is isolated by filtration. The filter residue is washed with cold methanol, filtered well with suction, and dried in a vacuum drying cabinet at 80° C.

Yield of spirophosphonate: 41.50 g (81% of theory) of a fine, white crystalline powder with a melting point of 246°–248° C.

Elemental analysis: calculated: C 32.82%, H 5.51%, P 24.19%; found: C 32.87%, H 5.60%, P 24.07%.

EXAMPLE 3

49.20 g (0.30 mole) of cyclohexanephosphonic acid are suspended in 80 ml of dioxane in a 350 ml sulfonating flask, equipped with stirrer, thermometer, dropping funnel and gas outlet pipe, and the suspension is heated to 70°–80° C. To the resultant solution is then added dropwise, over 15 minutes, a solution of cyclohexylphosphonic dichloride in 15 ml of dioxane. The evolution of HCl gas ensues at once, subsides after 2 hours, and is complete after 3 hours. Then 13.60 g (0.10 mole) of pentaerythritol are added in portions to the clear, pale yellow solution over 10 minutes. A clear solution forms, from which the spirophosphonate precipitates after a time. The suspension is cooled to room temperature and filtered. The filter residue is washed with a small amount of dioxane, well filtered with suction, and dried in a vacuum drying cabinet at 80° C.

Yield of spirophosphonate: 27.80 (70.9% of theory) of a white crystalline powder with a melting point of 297°–298.5° C.

Elemental analysis: calculated: C 52.04%, H 7.70%, P 15.79%; found: C 52.12%, H 7,76%, P 15.68%.

EXAMPLE 4

A 350 ml sulfonating flask, equipped with stirrer, thermometer, dropping funnel and gas outlet pipe, is charged with 94.80 g (0.60 mole) of phenylphosphonic acid and 100 ml of dioxane. Then 117 g (0.60 mole) of phenylphosphonic acid dichloride are added dropwise at 80° C. over 30 minutes. Vigorous evolution of HCl gas ensues immediately, subsides after 2 hours, and is complete after 3½ hours. To the clear, colourless solution are added, in portions, 27.20 g (0.20 mole) of pentaerythritol at 80°–90° C. over 15 minutes. The pentaerythritol goes into solution after a time. The suspension is cooled to room temperature and the product is collected by filtration. The filter residue is washed with dioxane, well filtered with suction, and dried in a vacuum drying cabinet at 80° C.

Yield of spirophosphonate: 58.10 g (76.45% of theory) of a white crystalline powder with a melting point of 266°–267° C.

Elemental analysis: calculated: C 53.69%, H 4.78%, P 16.29%; found: C 53.60%, H 4.82%, P 16.31%.

What is claimed is:

1. A process for the production of a diphosphaspiro compound of the formula

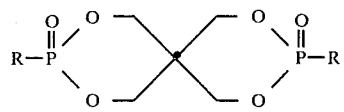  (I)

wherein each R independently is alkyl of 1 to 6 carbon atoms, phenyl, benzyl or cyclohexyl, which process comprises reacting a phosphonic acid or a phosphonic acid ester of the formula II

  (II)

wherein R has the same meaning as in formula I and each of R¹ R² is a hydrogen atom, methyl or ethyl, with a phosphonic acid dichloride of the formula III

  (III)

wherein R has the same meaning as in formula I, in equimolar amounts, in an inert organic solvent or using an excess of phosphonic acid ester of the formula II, in the temperature range from 50° to 120° C., to give ⅔ of the equimolar amount of reactant (II) or reactant III of a phosphonic anhydride of the formula IV $$(R-\overset{O}{\underset{\|}{P}}=O)_3,$$  (IV)

and subsequently reacting the anhydride of the formula IV with pentaerythritol, in the temperature range from 60° to 120° C., to a compound of the formula I, the molar ratio of anhydride of the formula IV to pentaerythritol being about 2:1.

2. A process according to claim 1, which comprises starting from compounds of the formula II and III, wherein both symbols R have the same meaning.

3. A process according to claim 1, which comprises starting from compounds of the formulae II and III, wherein each R is methyl.

4. A process according to claim 1, wherein the phosphonic anhydride of the formula IV is reacted with pentaerythritol without being isolated from the reaction solution.

* * * * *